United States Patent [19]

Edwards

[11] 4,110,332
[45] Aug. 29, 1978

[54] 1-TRIORGANOSTANNYL-3-ORGANOTHIO-4-SUBSTITUTED-1,2,4-DELTA²-TRIAZOLIDIN-5-ONES

[75] Inventor: Laroy H. Edwards, Napa, Calif.

[73] Assignee: Chevron Research Company, San Francisco, Calif.

[21] Appl. No.: 794,324

[22] Filed: May 5, 1977

[51] Int. Cl.² .................. C07F 7/22; A01N 9/12
[52] U.S. Cl. ..................... 260/299; 260/308 C; 560/16; 560/115; 560/148; 71/92; 71/67; 424/245
[58] Field of Search ......................... 260/299

[56] References Cited

U.S. PATENT DOCUMENTS

| 3,701,784 | 10/1972 | Seidel et al. | 260/308 R |
| 3,767,666 | 10/1973 | Zielinski | 260/308 C |
| 3,907,818 | 9/1975 | Büchel et al. | 260/299 |

FOREIGN PATENT DOCUMENTS 2,259,983 12/1971 Fed. Rep. of Germany.

OTHER PUBLICATIONS 2,250,572 4/1971 Fed. Rep. of Germany

Primary Examiner—Donald G. Daus
Assistant Examiner—Diana G. Rivers
Attorney, Agent, or Firm—Dix A. Newell; T. G. DeJonghe; Raymond Owyang

[57] ABSTRACT

Compounds of the formula

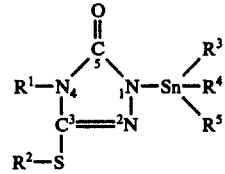

wherein $R^1$ is alkyl, alkenyl, cycloalkyl or aryl; $R^2$ is alkyl, haloalkyl, alkenyl or aryl; and $R^3$, $R^4$ and $R^5$ individually are alkyl or aryl, possess pesticidal activity.

6 Claims, No Drawings

1-TRIORGANOSTANNYL-3-ORGANOTHIO-4-SUBSTITUTED-1,2,4-DELTA²-TRIAZOLIDIN-5-ONES

RELATED APPLICATION

This application is related to applicant's copending application Ser. No. 617,871, filed Sept. 29, 1975, which is directed to fungicidal 1-halohydrocarbylthio-3-hydrocarbylthio-4-substituted-1,2,4-delta²-triazolidin-5-ones.

FIELD OF THE INVENTION

The present invention is directed to organotin compounds. Organotin compounds have been found to be useful in a variety of applications, such as for wood preservation, food packaging, marine anti-fouling paints, and as fungicides. A recent review of organotin compounds and their applications is found in an article by P. Smith and L. Smith, in Chem. Brit. 11, 208–211 (1975).

PRIOR ART STATEMENT

U.S. Pat. No. 3,907,818 of Buchel et al. discloses insecticidal and acaricidal trialkyl- and tricycloalkyl-stannyl-1,2,4-triazoles. The compounds of the invention are triorganostannyl-substituted 1,2,4-trazolidin-5-ones.

U.S. Pat. No. 3,767,666 of Zielinski discloses 3-hydrocarbylthio-1,4-disubstituted 1,2,4-triazol-2-in-5-ones, which are related to the 3-organothio-4-substituted-1,2,4-delta²-triazolidin-5-ones (3-organothio-4-substituted-1,2,4-triazol-2-in-5-ones) used as intermediates for the preparation of the compounds of the invention.

Arndt et al., Chemical Abstracts, Vol. 16 (1922), pg. 2509, discloses the methylation product of 4-phenylthiourazole (3-methylthio-4-phenyl-1,2,4-delta²-triazolidin-5-one), which is an intermediate for the preparation of the compounds of the invention.

DESCRIPTION OF THE INVENTION

The 1,2,4-delta²-triazolidin-5-ones of the invention are represented by the formula

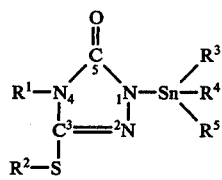

wherein $R^1$ is alkyl of 1 to 6 carbon atoms, alkenyl of 2 to 4 carbon atoms, cycloalkyl of 3 to 8 carbon atoms, phenyl, benzyl, or phenyl or benzyl substituted with 1 to 3 of the same or different substituents selected from fluoro, chloro, bromo, alkyl of 1 to 4 carbon atoms, haloalkyl of 1 to 4 carbon atoms and 1 to 3 chloro, bromo or fluoro, alkoxy of 1 to 3 carbon atoms, and nitro; $R^2$ is alkyl of 1 to 6 carbon atoms, alkenyl of 2 to 4 carbon atoms, haloalkyl of 1 to 4 carbon atoms and 1 to 5 of the same or different halogen atoms selected from fluoro, chloro and bromo, benzyl or benzyl substituted with 1 to 2 of the same or different substituents selected from fluoro, chloro, bromo, alkyl of 1 to 4 carbon atoms, alkoxy of 1 to 3 carbon atoms or nitro; and $R^3$, $R^4$ and $R^5$ individually are alkyl of 1 to 6 carbon atoms, phenyl, benzyl, or phenyl or benzyl substituted with 1 to 2 of the same or different substituents selected from fluoro, chloro, bromo or alkyl of 1 to 4 carbon atoms.

Preferably $R^1$ is alkyl of 1 to 4 carbon atoms, alkenyl of 2 to 3 carbon atoms, cycloalkyl of 5 to 6 carbon atoms, phenyl, benzyl, or phenyl or benzyl substituted with 1 to 2 substituents, either the same or different, selected from fluoro, chloro, bromo or alkyl of 1 to 4 carbon atoms. Most preferably $R^1$ is alkyl of 1 to 4 carbon atoms.

Preferably $R^2$ is alkyl of 1 to 6 carbon atoms, alkenyl of 2 to 3 carbon atoms, benzyl or benzyl substituted with 1 to 2 of the same or different substituents selected from fluoro, chloro, bromo or alkyl of 1 to 4 carbon atoms. Most preferably $R^2$ is alkyl of 1 to 4 carbon atoms.

Preferably $R^3$, $R^4$ and $R^5$ individually are alkyl of 1 to 6 carbon atoms, phenyl or benzyl.

Representative alkyl groups which $R^1$, $R^2$, $R^3$, $R^4$ and $R^5$ may represent are methyl, ethyl, propyl, isobutyl and n-butyl.

Representative alkenyl groups which $R^1$ and $R^2$ may represent are vinyl, allyl and 2-butenyl.

Representative cycloalkyl groups which $R^1$ may represent are cyclopropyl, cyclobutyl, cyclopentyl, cyclohexyl, 4-methylcyclohexyl and cyclooctyl.

Representative phenyl groups which $R^1$ may represent are:

halophenyls, such as
  o-fluorophenyl,
  p-fluorophenyl,
  p-chlorophenyl,
  o-chlorophenyl,
  m-chlorophenyl,
  m-bromophenyl,
  3,4-dichlorophenyl,
  3-chloro-4-bromophenyl,
  2,4,6-trichlorophenyl, and
  1,3,5-tribromophenyl;

alkylphenyls, such as
  p-tolyl,
  2,4-dimethylphenyl,
  3,5-diethylphenyl,
  4-isopropylphenyl, and
  3-n-butylphenyl;

haloalkylphenyls, such as
  2-chloromethylphenyl,
  3-(1',2'-dichloroethyl)phenyl,
  o-trichloromethylphenyl,
  p-trifluoromethylphenyl,
  n-tribromoethylphenyl, and
  2,4-ditrifluoromethylphenyl;

alkoxyphenyls, such as
  2-methoxyphenyl,
  4-ethoxyphenyl, and
  2,4-dipropoxyphenyl;

nitrophenyls, such as
  o-nitrophenyl,
  2,4-dinitrophenyl,
  p-nitrophenyl, and
  m-nitrophenyl;

phenyl substituted with different substituents, such as
  2-nitro-4-chlorophenyl,
  2-methyl-4-nitrophenyl, 3-methoxy-4-methylphenyl,
2,6-dimethyl-4-methoxyphenyl,
2-methyl-4-chlorophenyl,
2-bromo-4-ethylphenyl, and
3-chloro-4-isopropylphenyl.

Representative benzyl groups which $R^1$ and $R^2$ may represent are
4-chlorobenzyl,
2,4-dibromobenzyl,
4-methylbenzyl,
3-trifluoromethylbenzyl,
2-ethoxybenzyl, and
4-nitrobenzyl.

Representative haloalkyl $R^2$ groups are
chloromethyl,
difluoromethyl,
dichloromethyl,
dibromomethyl,
dichlorofluoromethyl,
trifluoromethyl,
tribromomethyl,
1,1,2,2-tetrafluoroethyl,
2,2,2-trichloroethyl,
1,2,2-trichloroethyl,
2,2,2-trichloroethyl,
1,1,2,2-tetrachloroethyl,
1-bromo-2,2,2-trichloroethyl,
pentachloroethyl,
pentabromomethyl,
3,4-dichlorobutyl, etc.

Representative alkenyl $R^2$ groups are allyl, 2-butenyl, 2-hexenyl, etc.

Representative phenyl and benzyl groups which $R^3$, $R^4$ and $R^5$ may represent are
o-fluorophenyl,
2,4-dichlorophenyl,
p-tolyl,
2-chloro-4-methylphenyl,
p-bromobenzyl, and
2,4-dimethylbenzyl.

The compounds of the present invention are prepared from an appropriate 1,2,4-delta$^2$triazolidin-5-one by reaction with a triorganotin halide, thus:

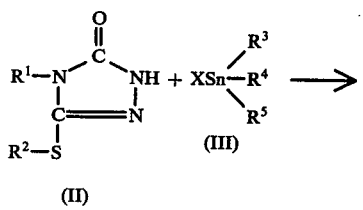

(1)

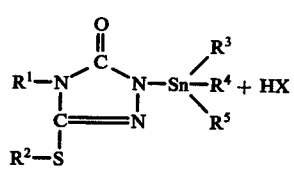

(I)

wherein $R^1$, $R^2$, $R^3$, $R^4$ and $R^5$ have the same meaning as stated before, and X is chloro or bromo, preferably chloro.

This reaction proceeds readily at temperatures in the range 0°–150° C, preferably 20°–100° C. Substantially equal molar quantities of the reactants are mixed in an inert solvent, preferably a chlorinated aliphatic hydrocarbon such as chloroform, dichloroethane or dichloromethane. Dichloromethane is preferred. A substantially equivalent amount of a base material is also present in the reaction medium to scavenge the hydrogen halide by-product. Such bases include triethylamine, pyridine, triethylene diamine, etc. The quantity of solvent varies, but is preferably sufficient to dissolve the triazolidin-5-one. In the case of compounds having low solubility, slurries in the solvent are satisfactory. Reaction times vary from 1 to 24 hours.

The product is isolated and purified by conventional procedures such as extraction, filtration and crystallization.

The 3-organothio-4-substituted-1,2,4-delta$^2$-triazolidin-5-one (II) utilized in the above reaction is in turn obtained from the cyclization of an appropriate 1-carbomethoxy-4-substituted thiosemicarbazide (IV) under the influence of a base and subsequent alkylation, thus:

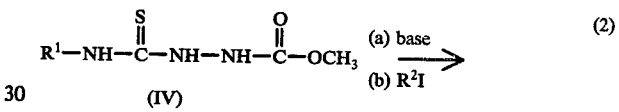

(2)

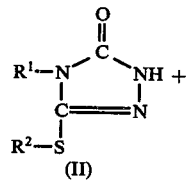

(II)

wherein $R^1$ and $R^2$ are as indicated above.

The preferred base is potassium carbonate, and for satisfactory yields it is necessary that an exact equivalent, (i.e., one half mol) be used. This reaction is carried out in a polar solvent, preferably methanol or ethanol. The temperature of the reaction is in the range 50°–100° C; preferably it is the atmospheric pressure reflux temperature of the solvent. Reaction is carried out until all of the carbonate has reacted, as indicated by its disappearance. Then a slight molar excess of the iodide reactant ($R^2$I) is added. The crude reaction mixture is concentrated, mixed with water and extracted with dichloromethane. After drying, the dichloromethane is removed by distillation under reduced pressure. The crude product obtained in this way is satisfactory for the next step of the synthesis. However, it may be purified by crystallization from a benzene/hexane mixed solvent system.

The starting material (IV) for reaction (2) is readily obtained from the room-temperature reaction of methylhydrazinocarboxylate (V) with an appropriate isothiocyanate (VI) in a solvent such as diethylether:

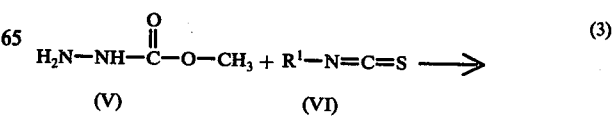

(3)

-continued

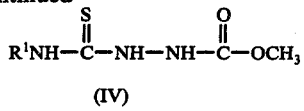

(IV)

After a reaction time of 15 to 150 minutes, the product precipitates from the ether solvent and is readily recovered by cooling and filtration. No purification other than drying is required; the product is ready for use in reaction (2).

UTILITY

The compounds of the invention have exhibited pesticidal activity against a variety of microbiological organisms, such as fungi, molds and bacteria. The compounds of the invention are particularly effective for the control of fungi.

When used as pesticides against microbiological organisms and pests such as fungi and bacteria, the compounds are applied in pesticidally (fungicidally or bactericidally) effective amounts to the organism and/or their habitats, such as vegetative hosts and non-vegetative hosts, e.g., animal products. Generally, some pesticidal compounds will be more pesticidally active than others against particular fungi or bacteria. The amount of pesticidal compound used will, of course, depend on several factors such as the host, the type of fungus and the particular compound of the invention. As with most pesticidal compounds, the pesticides of the invention are not usually applied full strength, but are generally incorporated with conventional biologically inert extenders or carriers normally employed for facilitating dispersion of active pesticidal compounds, recognizing that the formulation and mode of application may affect the activity of the pesticide. Thus, the pesticides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5-80% pesticide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1 to 15% by weight of the pesticidal composition.

Dusts are freely flowing admixtures of the active pesticide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant. Useful liquid concentrates include the emulsifiable concentrates which are homogeneous liquid or paste compositions which are readily dispersed in water or other dispersants, and may consist entirely of the pesticide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for pesticidal applications include simple solutions of the active pesticide in a dispersant in which it is completely soluble at the desired concentration, such as acetone, alkylated naphthalenes, xylene, or other organic solvents. Granular formulations, wherein the pesticide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying pesticides are well known in the art.

The percentages by weight of the pesticide may vary according to the manner in which the composition is to be applied and the particular type of formulation, but in general comprise 0.5 to 95% of the pesticide by weight of the pesticidal composition.

The pesticidal compositions may be formulated and applied with other active ingredients, including other fungicides, insecticides, nematocides, bactericides, plant growth regulators, fertilizers, etc.

The compounds of this invention are also toxic to a variety of crop and household insects. It is generally desirable to apply the compounds in insecticidal compositions comprising one or more of the insecticidal compounds intimately admixed with a biologically inert carrier. The carrier may be a liquid or a solid, e.g., the compounds of the invention may be formulated as solutions, emulsifiable concentrates, wettable powders, powdery dusts or granules, as hereinbefore described for other pesticidal compositions of the compounds of the invention. In insecticidal compositions, the insecticidal compounds can be from about 0.01 to 95% by weight of the entire composition.

The insecticidal compositions may be formulated and applied with other active ingredients, including other nematocides, insecticides, fungicides, bactericides, plant growth regulators, fertilizers, etc. In applying the chemical, an insecticidally effective amount and concentration of the compounds of this invention is, of course, employed.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insecta, but also to other related classes of arthropods whose members are segmented invertebrates having more or fewer than six legs, such as spiders, mites, ticks, centipedes, worms, and the like.

The compounds of the present invention are also useful as herbicides in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally, for both pre- and post-emergent control, the herbicidal compounds of the invention are applied at rates of 0.2 to 60 kg/ha, and the preferred rate is in the range 0.5 to 40 kg/ha.

The compounds of the invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, streams, canals, pools and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water 1 foot deep, 0.1 to 10 ppm is equal to about 0.3 to 30 pounds per acre of water 1 foot deep. These compounds may be applied to the aqueous growth environments of such organisms as dispersible powders or in solution with water-miscible solvents.

EXAMPLES

Example 1A — Preparation of 1-tri-n-butylstannyl-3-methylthio-4-methyl-1,2,4-delta$^2$-triazolin-5-one A mixture of 26.5 g (0.18 mol) 1-carbomethoxy-4-methylthiosemicarbazide, 13.8 g potassium carbonate and 200 ml g of methanol was heated under reflux for 1.5 hours to obtain a clear solution. Iodomethane (25.9 g) was added to the reaction mixture and heated under reflux an additional 3 hours. The reaction mixture was then cooled, filtered and evaporated under reduced pressure. The residue was washed with water, dissolved in dichloromethane, dried over magnesium sulfate and evaporated under reduced pressure. The residue was crystallized from petroleum ether to 3-methylthio-4-methyl-1H-1,2,4-delta$^2$-triazolin-5-one, m.p. 87°–90° C. Elemental analysis for $C_4H_7N_3OS$ showed: % wt. S, calc. 22.11, found 21.1.

A 6.0-g (0.06 mol) sample of triethylamine was added slowly to a solution of 7.3 g (0.05 mol) 3-metylthio-4-methyl-1H-1,2,4-delta$^2$-triazolin-5-one and 16.3 g (0.05 mol) chlorotri-n-butyltin in 200 ml dichloromethane. The reaction mixture was heated under reflux for 3 hours, cooled, filtered, and evaporated under reduced pressure. The resulting residue was diluted with petroleum ether and filtered. The filtrate was evaporated under reduced pressure to give the product as a white solid, m.p. 64°–65° C. The product and its elemental analysis are tabulated in Table I as Compound No. 1.

Example 1B — Preparation of 1-triphenylstannyl-3-allylthio-4-methyl-1,2,4-delta$^2$-triazolidin-5-one A solution of 5.1 g (0.03 mol) 3-allylthio-4-methyl-1H-1,2,4-delta$^2$-triazolidin-5-one, 11.6 g (0.03 mol) chlorotriphenyltin and 3.0 g (0.03 mol) triethylamine in 100 ml dichloromethane was heated under reflux for 6 hours, cooled and washed with water. The organic phase was dried over magnesium sulfate and evaporated under reduced pressure. The residue was crystallized from petroleum ether to give the product as a white solid, m.p. 61°–64° C. The product and its elemental analysis are tabulated in Table I as Compound No. 6.

The compounds tabulated in Table I were prepared by a procedure essentially identical to that of Examples 1A–1B. The structure of each compound tabulated in Table I was confirmed by infrared spectral analysis and/or nuclear magnetic resonance spectroscopy.

Example 2 — Mycelia Inhibition

The compounds of the present invention were evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were inoculated with the particular mycelium growth by covering the paper with a potato dextrose broth culture of mycelial suspension. The inoculated papers were then placed on potato dextrose agar plates and sprayed by means of a microsprayer with the fungicidal solution. The treated paper strips were incubated at 25° C and data are taken after 24 hours. Fungicidal activities are measured by a zone of inhibited mycelial growth from the center of the paper strip. The effectiveness of the compounds tested for fungicidal activity is reported in Table II in terms of micrograms/cm$^2$ for 99% control of the fungus.

Example 3 — Bacterial Inhibition

The compounds of the present invention were evaluated for bactericidal effectiveness by means of an in-vitro bacterial inhibition test. This test is designed to measure the bactericidal activity of chemicals in terms of their degree of inhibition of bacterial growth. Each compound to be tested was dissolved in acetone to 500 ppm concentration. Bacterial suspensions were prepared by washing a culture of the desired bacterium from an agar medium with sterile water into a vessel and further diluting the aqueous suspension with sterile water to a predetermined bacterial density (measured by light-blocking effect of bacterial cells in a spectophotometer). This diluted bacterial suspension was sprayed onto agar test plates. The inoculated agar plates were then sprayed by means of a microsprayer with the acetone solution of the test compound and incubated at 23.5° C for 24 hours. Bacterial activities were then measured by a zone of inhibited bacterial growth from the center of the plate. The effectiveness of the compounds tested for bactericidal activity is reported in Table III in terms of micrograms/cm$^2$ for 99% control of the bacteria.

Example 4 — Insect Control

The compounds of this invention were tested as follows to illustrate their insecticidal activity. Test results are reported in Table IV.

TEST PROCEDURES

Houseflies (*Musca domestica L.*): A 500-ppm acetone solution of the test compound was placed in a microsprayer (atomizer). A random mixture of anesthetized male and female flies was placed in a container and 55 mg of the above-described acetone solution was sprayed on it. A lid was placed on the container. A mortality reading was made after 24 hours.

Aphids (*Aphis gossypii* Glover): An acetone solution of the test compound containing a small amount of nonionic emulsifier was diluted with water to 40 ppm. Cucumber leaves infested with the cotton aphids were dipped in the toxicant solution. Mortality readings were then taken after 24 hours.

American cockroach (*Periplaneta americana L.*): A 500-ppm acetone solution of the test compound was placed in a microsprayer (atomizer). A random mixture of anesthetized male and female roaches was placed in a container and 55 mg of the above-described acetone solution was sprayed on it. A lid was placed on the container. A mortality reading was made after 24 hours.

Cabbage looper (*trichoplusia ni*): An acetone solution of the test compound containing a small amount of nonionic emulsifier was diluted with water to 500 ppm. Cucumber leaf sections were dipped in the toxicant solution and dried. The sections were then infested with cabbage looper larvae. Mortality readings were taken after 24 hours.

Two-spotted mites (*Tetramuchus urticae*): Pinto bean leaves were infested with two-spotted mites. The mites were then allowed to lay eggs on the leaves. After 48 hours, the leaves were dipped into a water/acetone solution containing a small amount of a nonionic surfactant and 40 ppm of the test compound. The treated leaves were then maintained at 85° F. One day after treatment the mortality of adult mites was determined, and seven days after treatment the egg mortality (non-hatching eggs) was determined.

Example 5 — Herbicidal Tests

Post-emergent herbicidal tests with representative compounds of this invention were made using the following method.

An acetone solution of the test compound was prepared by mixing 750 mg of the compound, 220 mg of a nonionic surfactant and 25 ml of acetone. This solution was added to approximately 125 ml of water containing 156 mg of surfactant.

This test solution was uniformly sprayed on two similar pots of 24-day-old plants (approximately 15 to 25 plants per pot) at a dose of 33 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table V.

Example 6 — Alga Control

Representative compounds of the invention were tested as algicides by the following method. The alga test species were Lemna, Elodea and Spirolina. An acetone solution of the test compound and a small amount of an alkylarylpolyoxyethylene glycol-containing surfactant was prepared. This solution was mixed with a nutrient broth in a quantity sufficient to give a concentration of 2 ppm. A 240-ml container was filled with this mixture. A sample of the test alga was added to each container and the container was then placed in an illuminated environment and maintained at a temperature of about 20° C for incubation. The containers were observed periodically for alga growth (as compared to an untreated check). The algicidal effectiveness of the test compound was determined based on a final observation of alga growth after 7 to 10 days. The results of the test on a 0-to-100 basis — 0 indicating no effectiveness and 100 indicating complete effectiveness — are reported in Table VI.

TABLE I

Compounds of the formula:

$$R^1-N\underset{\underset{S}{|}}{\overset{\overset{O}{\|}}{\underset{|}{C}}}-N-Sn\begin{matrix}R^3\\R^4\\R^5\end{matrix}$$
$$\phantom{R^1-N}C=N$$
$$\phantom{R^1-N}|$$
$$\phantom{R^1-N}R^2-S$$

| No. | $R^1$ | $R^2$ | $R^3$, $R^4$ and $R^5$ | Melting Point, °C | Sulfur Analysis Calc. | Sulfur Analysis Found |
|---|---|---|---|---|---|---|
| 1 | $CH_3$ | $CH_3$ | $n-C_4H_9$ | 64–65 | 7.4 | 6.9 |
| 2 | $\phi$ | $CH_3$ | $n-C_4H_9$ | 42–44 | 6.5 | 6.6 |
| 3 | $CH_3$ | $CH_2=CHCH_2$ | $n-C_4H_9$ | 44–45 | 7.0 | 6.9 |
| 4 | $CH_3$ | $C_2H_5$ | $n-C_4H_9$ | 69–70 | 7.2 | 7.4 |
| 5 | $CH_3$ | $n-C_3H_7$ | $n-C_4H_9$ | 64–65 | 6.9 | 7.3 |
| 6 | $CH_3$ | $CH_2=CHCH_2$ | $\phi$ | 61–64 | 6.2 | 5.6 |
| 7 | $CH_3$ | $\phi CH_2$ | $n-C_4H_9$ | 61–62 | 6.3 | 6.4 |
| 8 | $2,4-Cl_2-\phi$ | $CH_3$ | $n-C_4H_9$ | 65–66 | 5.7 | 5.9 |
| 9 | cyclohexyl | $CH_3$ | $n-C_4H_9$ | oil | 6.4 | 5.7 |

$\phi$ = phenyl

TABLE II

Mycelia Inhibition, micrograms/cm² for 99% control

| Compound No. | (1) | (2) | (3) | (4) | (5) |
|---|---|---|---|---|---|
| 1 | 0.7 | 0.5 | 0.5 | 0.6 | 0.8 |
| 2 | 0.8 | 0.3 | 0.2 | 0.9 | 0.4 |
| 3 | 1.2 | 0.2 | 0.3 | 0.7 | — |
| 4 | 0.8 | 0.2 | 0.3 | 0.9 | 0.3 |
| 5 | 1.2 | 0.2 | 0.4 | 0.7 | 0.3 |
| 6 | 0.4 | 0.5 | 0.5 | 0.8 | 1.2 |
| 7 | 1.1 | 0.3 | 1.0 | 0.5 | 0.5 |
| 8 | — | 0.2 | 0.2 | 0.7 | 0.5 |
| 9 | 0.2 | >1.7 | 0.3 | 0.3 | 0.2 |

(1) = Pythium ultimun
(2) = Rhizoctonia solani
(3) = Aspergillus niger
(4) = Fusarium moniloforma
(5) = Botrytis cinerea

TABLE III

Bacterial Inhibition micrograms/cm² for 99% control

| Compound No. | (1) | (2) | (3) |
|---|---|---|---|
| 1 | 0.5 | 0.1 | 0.3 |
| 2 | 0.2 | 0.2 | 0.6 |
| 3 | >1.7 | >1.7 | >1.7 |
| 4 | >1.7 | >1.7 | 0.2 |
| 5 | >1.7 | >1.7 | 0.1 |
| 6 | >1.7 | >1.7 | >1.7 |
| 7 | >1.7 | >1.7 | >1.7 |
| 8 | 0.2 | >1.7 | 0.2 |
| 9 | >1.7 | >1.7 | >1.7 |

(1) = Pseudomonas syringae
(2) = Erwinia amylovora
(3) = Xanthomonas ulsicatoria

TABLE IV

Percent Insect Mortality

| Compound No. | (1) | (2) | (3) | (4) | (5) | (6) |
|---|---|---|---|---|---|---|
| 1 | 90 | 30 | 60 | 100 | 90 | 70 |
| 2 | 0 | 100 | 0 | 100 | 100 | 100 |
| 3 | 78 | 78 | 0 | 100 | 100 | 100 |
| 4 | 78 | 100 | 50 | 100 | 99 | 100 |
| 5 | 39 | 98 | 0 | 100 | 100 | 100 |
| 6 | 0 | 0 | 0 | 0 | 0 | 0 |
| 7 | 22 | 39 | 10 | 100 | 94 | 100 |
| 8 | 0 | 0 | — | 100 | 100 | 100 |
| 9 | 70 | 39 | 30 | 100 | 100 | 99 |

(1) = Flies
(2) = Aphids
(3) = Cockroaches
(4) = Cabbage loopers
(5) = Mites
(6) = Mite eggs

TABLE V

Herbicidal Effectiveness

| Compound No. | O | W | C | M | P | L |
|---|---|---|---|---|---|---|
| 1 | 15 | 95 | 40 | 100 | 100 | 90 |
| 2 | 90 | 100 | 90 | 100 | 100 | 100 |
| 3 | 30 | 95 | 60 | 100 | 100 | 100 |
| 4 | 50 | 97 | 50 | 100 | 100 | 100 |
| 5 | 55 | 100 | 70 | 100 | 100 | 100 |
| 6 | 0 | 0 | 0 | 100 | 98 | 95 |
| 7 | 45 | 95 | 85 | 100 | 100 | 98 |
| 8 | 45 | 90 | 75 | 100 | 100 | 95 |
| 9 | 70 | 98 | 60 | 100 | 100 | 100 |

L = Lambsquarter (Chenopodium album)
M = Mustard (Brassica arvensis)
P = Pigweed (Amaranthus retroflexus)
C = Crabgrass (Digitaria sanquinalis)
W = Watergrass (Echinochloa crusgalli)
O = Wild Oats (Avena fatua)

TABLE VI

Percent Aquatic Weed Control

| Compound No. | (1) | (2) | (3) |
|---|---|---|---|
| 1 | 100 | 99 | 98 |
| 2 | 90 | 100 | 100 |
| 3 | 60 | 100 | 99 |
| 4 | 80 | 100 | 100 |
| 5 | 80 | 100 | 100 |
| 6 | 0 | 96 | 100 |
| 7 | 0 | 78 | 78 |
| 8 | 100 | 100 | 100 |
| 9 | 100 | 100 | 94 |

(1) = Spirolina
(2) = Lemna
(3) = Elodea

What is claimed is:

1. A compound of the formula

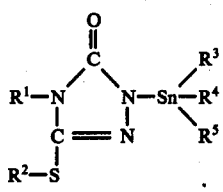

wherein $R^1$ is alkyl of 1 to 4 carbon atoms, alkenyl of 2 to 3 carbon atoms, cycloalkyl of 5 to 6 carbon atoms, phenyl or benzyl substituted with 1 to 2 of the same or different substituents selected from fluoro, chloro, bromo and alkyl of 1 to 4 carbon atoms; $R^2$ is alkyl of 1 to 4 carbon atoms, alkenyl of 2 to 3 carbon atoms, benzyl or benzyl substituted with 1 to 2 of the same or different substituents selected from fluoro, chloro, bromo and alkyl of 1 to 4 carbon atoms; and $R^3$, $R^4$ and $R^5$ individually are alkyl of 1 to 6 carbon atoms, phenyl or benzyl.

2. The compound of claim 1 wherein $R^1$ is alkyl of 1 to 4 carbon atoms, $R^2$ is alkyl of 1 to 4 carbon atoms and $R^3$, $R^4$ and $R^5$ individually are alkyl of 1 to 6 carbon atoms.

3. The compound of claim 1 wherein $R^1$ and $R^2$ are methyl, and $R^3$, $R^4$ and $R^5$ are n-butyl.

4. The compound of claim 1 wherein $R^3$, $R^4$ and $R^5$ individually are alkyl of 1 to 6 carbon atoms.

5. The compound of claim 1 wherein $R^1$ is alkyl of 1 to 4 carbon atoms.

6. The compound of claim 1 wherein $R^2$ is alkyl of 1 to 4 carbon atoms.

* * * * *